United States Patent
Kleyman et al.

(10) Patent No.: US 9,017,252 B2
(45) Date of Patent: Apr. 28, 2015

(54) ACCESS ASSEMBLY WITH FLEXIBLE CANNULAS

(75) Inventors: Gennady Kleyman, Brooklyn, NY (US); Gregory G. Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 138 days.

(21) Appl. No.: 13/030,172

(22) Filed: Feb. 18, 2011

(65) Prior Publication Data

US 2011/0251466 A1   Oct. 13, 2011

Related U.S. Application Data

(60) Provisional application No. 61/323,092, filed on Apr. 12, 2010.

(51) Int. Cl.
| | |
|---|---|
| *A61B 1/32* | (2006.01) |
| *A61B 17/34* | (2006.01) |
| *A61B 17/00* | (2006.01) |
| *A61B 17/29* | (2006.01) |

(52) U.S. Cl.
CPC ......... *A61B 17/3423* (2013.01); *A61B 17/3474* (2013.01); *A61B 17/3498* (2013.01); *A61B 2017/00858* (2013.01); *A61B 2017/00907* (2013.01); *A61B 2017/2905* (2013.01); *A61B 2017/3441* (2013.01); *A61B 2017/3445* (2013.01); *A61B 2017/347* (2013.01); *A61B 2017/3429* (2013.01); *A61B 2017/3466* (2013.01)

(58) Field of Classification Search
CPC .......... A61B 17/02; A61B 2017/0287; A61B 17/0293; A61B 17/0281
USPC ................................ 600/192, 194, 200–249
See application file for complete search history.

(56) References Cited

U.S. PATENT DOCUMENTS

| | | | |
|---|---|---|---|
| 3,583,170 A | * | 6/1971 | DeVries ....................... 405/162 |
| 4,016,884 A | | 4/1977 | Kwan-Gett |
| 5,312,417 A | | 5/1994 | Wilk |
| 5,391,156 A | | 2/1995 | Hildwein et al. |
| 5,480,410 A | | 1/1996 | Cuschieri et al. |
| 5,904,703 A | | 5/1999 | Gilson |
| 5,906,577 A | * | 5/1999 | Beane et al. .................. 600/207 |
| 6,048,309 A | | 4/2000 | Flom et al. |

(Continued)

FOREIGN PATENT DOCUMENTS

| | | |
|---|---|---|
| CA | 2702419 | 11/2010 |
| CN | 101401742 A | 4/2009 |

(Continued)

OTHER PUBLICATIONS

European Search Report 11194126.6-2310 dated Feb. 5, 2012.

(Continued)

*Primary Examiner* — Matthew Lawson

(57) ABSTRACT

An access assembly configured to receive one or more surgical instruments is provided. The access assembly includes a compressible port having a proximal end and a distal end, the port defining a plurality of longitudinal passageway extending from the proximal end to the distal end and a flexible cannula assembly received in each of the longitudinal passageway of the port. The cannula assemblies each including a seal configured to receive an instrument inserted therethrough in a sealing manner.

9 Claims, 5 Drawing Sheets

(56) References Cited

U.S. PATENT DOCUMENTS

| | | | |
|---|---|---|---|
| 6,162,196 | A | 12/2000 | Hart et al. |
| 6,454,783 | B1 | 9/2002 | Piskun |
| 6,551,270 | B1* | 4/2003 | Bimbo et al. .............. 604/93.01 |
| 6,562,022 | B2 | 5/2003 | Hoste et al. |
| 6,929,637 | B2 | 8/2005 | Gonzalez et al. |
| 7,011,645 | B2 | 3/2006 | McGuckin, Jr. et al. |
| 7,014,628 | B2 | 3/2006 | Bousquet |
| 7,052,454 | B2 | 5/2006 | Taylor |
| 7,217,277 | B2 | 5/2007 | Parihar et al. |
| 7,300,399 | B2 | 11/2007 | Bonadio et al. |
| 7,344,547 | B2 | 3/2008 | Piskun |
| 7,473,221 | B2 | 1/2009 | Ewers et al. |
| 7,559,893 | B2 | 7/2009 | Bonadio et al. |
| 7,753,901 | B2 | 7/2010 | Piskun et al. |
| 7,758,500 | B2 | 7/2010 | Boyd et al. |
| 7,766,824 | B2 | 8/2010 | Jensen et al. |
| 7,787,963 | B2 | 8/2010 | Geistert et al. |
| 7,798,898 | B2 | 9/2010 | Luciano, Jr. et al. |
| 7,798,998 | B2 | 9/2010 | Thompson et al. |
| 8,157,786 | B2 | 4/2012 | Miller et al. |
| 8,187,177 | B2 | 5/2012 | Kahle et al. |
| 8,187,178 | B2 | 5/2012 | Bonadio et al. |
| 2003/0014076 | A1 | 1/2003 | Mollenauer et al. |
| 2003/0028179 | A1* | 2/2003 | Piskun ............................ 606/1 |
| 2003/0093104 | A1 | 5/2003 | Bonner et al. |
| 2004/0138529 | A1 | 7/2004 | Wiltshire et al. |
| 2006/0020241 | A1* | 1/2006 | Piskun et al. .............. 604/93.01 |
| 2006/0149306 | A1 | 7/2006 | Hart et al. |
| 2006/0161049 | A1 | 7/2006 | Beane et al. |
| 2006/0247499 | A1 | 11/2006 | Butler et al. |
| 2006/0247500 | A1 | 11/2006 | Voegele et al. |
| 2006/0247516 | A1 | 11/2006 | Hess et al. |
| 2006/0247673 | A1 | 11/2006 | Voegele et al. |
| 2006/0247678 | A1 | 11/2006 | Weisenburgh, II et al. |
| 2006/0270911 | A1 | 11/2006 | Voegele et al. |
| 2007/0208312 | A1 | 9/2007 | Norton et al. |
| 2008/0027476 | A1 | 1/2008 | Piskun |
| 2008/0097332 | A1 | 4/2008 | Greenhalgh et al. |
| 2008/0161826 | A1 | 7/2008 | Guiraudon |
| 2008/0255519 | A1 | 10/2008 | Piskun et al. |
| 2009/0012477 | A1 | 1/2009 | Norton et al. |
| 2009/0093683 | A1* | 4/2009 | Richard et al. ................. 600/204 |
| 2009/0093752 | A1 | 4/2009 | Richard et al. |
| 2009/0187079 | A1 | 7/2009 | Albrecht et al. |
| 2009/0227843 | A1 | 9/2009 | Smith et al. |
| 2009/0326332 | A1 | 12/2009 | Carter |
| 2010/0063452 | A1 | 3/2010 | Edelman et al. |
| 2010/0113882 | A1* | 5/2010 | Widenhouse et al. ........ 600/208 |
| 2010/0240960 | A1* | 9/2010 | Richard ........................ 600/208 |
| 2010/0274093 | A1* | 10/2010 | Shelton, IV ................... 600/206 |
| 2010/0280326 | A1 | 11/2010 | Hess et al. |
| 2010/0298646 | A1 | 11/2010 | Stellon et al. |
| 2010/0312063 | A1* | 12/2010 | Hess et al. .................... 600/204 |
| 2011/0054260 | A1 | 3/2011 | Albrecht et al. |

FOREIGN PATENT DOCUMENTS

| | | |
|---|---|---|
| EP | 0950376 | 10/1999 |
| EP | 1312318 | 5/2003 |
| EP | 1 774 918 A1 | 4/2007 |
| EP | 2044889 | 4/2009 |
| EP | 2226025 | 9/2010 |
| EP | 2229900 | 9/2010 |
| EP | 2253283 | 11/2010 |
| WO | WO 97/33520 | 9/1997 |
| WO | WO 99/16368 | 4/1999 |
| WO | WO2004/054456 | 7/2004 |
| WO | WO 2008/042005 | 4/2008 |
| WO | WO2010/141409 | 12/2010 |

OTHER PUBLICATIONS

European Search Report 11250792.6-2310 dated Feb. 24, 2012.
European Search Report 11250452 dated Nov. 22, 2013.
Chinese Office Action Application No. 201110093584.8 dated Jan. 4, 2015.

* cited by examiner

ACCESS ASSEMBLY WITH FLEXIBLE CANNULAS

CROSS REFERENCE TO RELATED APPLICATION

The present application claims the benefit of and priority to U.S. Provisional Application Ser. No. 61/323,092 filed on Apr. 12, 2010, the entire contents of which are incorporated herein by reference.

BACKGROUND

1. Technical Field

The present disclosure relates to assemblies for accessing a body cavity through an opening. More particularly, the present disclosure relates to an access assembly including flexible cannulas for accessing a body cavity.

2. Background of Related Art

Methods and apparatus for performing closed surgical procedures are known. Such procedures greatly reduce postoperative recovery time and minimize scarring to the patient. These procedures typically involve inserting one or more access assemblies through the abdominal wall of the patient and insufflating the abdominal cavity. A laparoscope or other viewing instrument is inserted through one of the access assemblies, or directly through the abdominal wall, to provide the clinician with an image of the abdominal cavity. The surgeon is then able to perform the procedure within the abdominal cavity by manipulating instruments that have been extended through the access assemblies.

One such access assembly is described in U.S. patent application Ser. No. 12/224,024, filed Oct. 2, 2008, the disclosure of which is incorporated herein by reference in its entirety. The '024 application discloses an access assembly that includes a compressible port and a plurality of cannula assemblies extending through the port. In one embodiment, the compressible port defines a substantially hourglass shaped member configured to be selectively received with an incision to provide access to a body cavity. The cannula assemblies received through the compressible port are generally rigid with a valve assembly located on a proximal end thereof. Each valve assembly is configured to receive an instrument therethrough in a sealing manner and is configured to create a seal in the absence of an instrument received therethrough. The rigidity of the cannula assemblies limits the type, size and function of the instruments inserted therethrough. Furthermore the rigidity of the cannulas necessitates staggering of the cannula assemblies when more than one cannula is received therethrough as the valve assemblies prevent alignment of the rigid cannulas.

Therefore it would be beneficial to have an access assembly that includes a compressible port and a plurality of flexible cannulas operably engaged therewith to increase the options available to a surgeon.

SUMMARY

An access assembly for insertion through tissue is provided. The access assembly includes a compressible port having a proximal end and a distal end. The port defines a plurality of longitudinal lumen extending from the proximal end to the distal end. The access assembly further includes flexible cannula assemblies received within the lumen of the port, each cannula assembly being configured to receive an instrument inserted therethrough in a sealing manner.

The compressible port includes a central portion and an upper rim at a proximal end of the central portion. The port may further include a lower rim at a distal end of the central portion. The upper rim may have a diameter greater than a diameter of the central portion. The plurality of cannula assembly may be securely attached to the port. The port may include a parylene coating. Each of the cannula assemblies may include a seal configured to seal the lumen in the absence of an instrument being inserted therethrough.

In one embodiment, the cannula assemblies include zero-closure or duck-bill seals. The cannula assemblies may be over-molded to the compressible port. The cannula assemblies may be securely attached to the compressible port. The cannula assemblies may extend completely through the compressible port, may extend less than completely therethrough or may extend so as to be substantially flush with a distal face of the compressible port.

DESCRIPTION OF THE DRAWINGS

Embodiments of the access assembly are disclosed herein with reference to the drawings, wherein.

DETAILED DESCRIPTION

An embodiment of the presently disclosed access assembly will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user. Although the access assembly of the present disclosure will be described as relates to a procedure performed through an incision in the abdominal wall to access the abdominal cavity, it is envisioned that the access assemblies of the present disclosure may be used to access various cavities within the body through an incision or through naturally occurring orifices or opening, i.e., anus or vagina. While the use of the compressible port is often described herein as engaging an incision, it should be recognized that this is merely exemplary and is not intended to limit the use of the port in any way, but rather it should be recognized that the present invention is intended to be useable in all instances in situations in which the port engages an incision, a naturally occurring orifice, or any other suitable opening.

Figure 1:
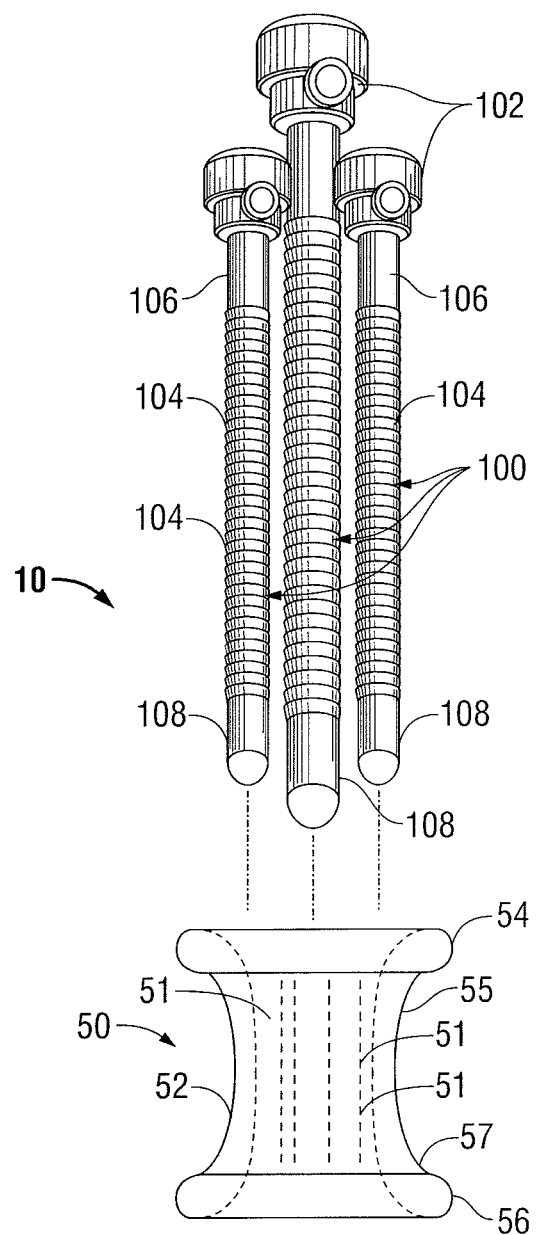
FIG. 1 is an exploded side view of an embodiment of an access assembly according to the aspects of the present disclosure.

Referring to FIG. 1 there is disclosed an access assembly 10 for use in single incision surgery. Access assembly 10 includes a compressible port 50 and a plurality of flexible cannula 100. Port 50 is flexible or compressible to allow insertion through an incision in the body of a patient such that after insertion it will expand within the incision and seal the opening. Additionally, the flexible nature of port 50 allows surgical instruments inserted therethrough to be manipulated about their axes and thus allow a higher degree of movement of the surgical instruments to orient them relative to the tissue being operated upon. The flexible nature of cannula assemblies 100 permit cannula assemblies 100 to conform to a curve or bend in an instrument inserted therethough. The flexibility of cannula assemblies 100 further permit the alignment of the cannula within and through compressible port 50 as valve assemblies 102 located on the proximal ends thereof may be deflected away from one another.

Still referring to FIG. 1, compressible port 50 includes a plurality of longitudinal passageways or lumen 51 (shown in phantom) extending therethrough configured to receive cannulas 100. Port 50 may be formed of various materials such as, for example, silicone, thermoplastic elastomers (TPE), rubber, foam, gel, etc. In this manner, compressible port 50 may be compressed or squeezed and inserted through an incision in the body of a patient. In one embodiment, compressible port 50 includes TPE material that is infused with an inert gas, e.g. $CO_2$ or Nitrogen, to form a foam structure. Compressible port 50 may be coated with a lubricant, e.g. Parylene N or C, in order to create a lubricious surface finish on all external surfaces. The coating may help facilitate insertion of port 50 into an incision.

With reference still to FIG. 1, compressible port 50 may include a central portion 52 having an upper rim 54 located at a proximal end 55 of central portion 52 and a lower rim 56 located at a distal end 57 of central portion 52. Upper rim 54 and lower rim 56 aid in preventing movement of compressible port 50 longitudinally through an incision in the patient. Compressible port 50 may be sized and dimensioned for use through tissue of various thicknesses and/or in opening of various sizes.

Figure 2:
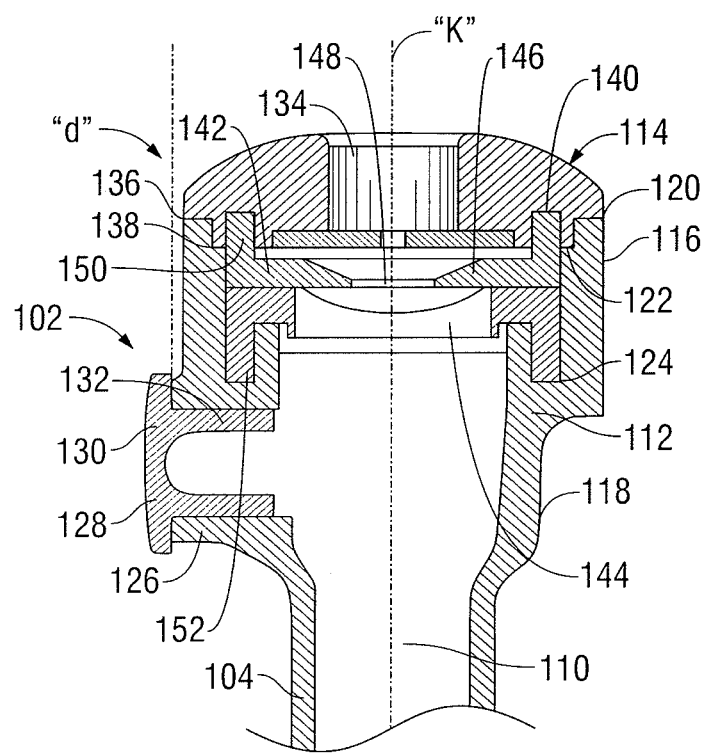
FIG. 2 is a cross-sectional side view of a proximal end of a cannula assembly of the access assembly of FIG. 1.

With reference now to FIGS. 1 and 2, each cannula assembly 100 includes cannula head or valve assembly 102 and cannula sleeve 104 connected to the housing 102. Cannula sleeve 104 defines a longitudinal axis "k" extending along the length of the cannula sleeve 104 and has proximal (or trailing) and distal (or leading) ends 106, 108. Cannula sleeve 104 may be formed of elastomers, including thermoplastic elastomers, silicone, urethane, polyisoprene, nitrile, later EPDM and flouroelastomer, or other suitable material. In one embodiment, cannula sleeve 104 is formed to be flexible, e.g., of Santoprene 281-87 MED and includes an 87 Shore A durometer. As shown, cannula sleeve 104 may include ribs on an outer surface thereof. These ribs may provide for improved fixation of the cannula in lumen 51, and may also provide an accordion-type configuration to improve the flexibility of the cannula. Cannula sleeve 104 may be transparent or opaque. The diameter of cannula sleeve 104 may vary, but, typically ranges from about 3 millimeters (mm) to about 18 mm. In one embodiment, the diameter of cannula sleeve 104 is about 5 mm. Cannula sleeve 104 and cannula head 102 further define internal longitudinal passage 110 extending through the cannula sleeve 104 and the cannula head 102 is dimensioned to permit passage of surgical instrumentation.

With particular reference to FIG. 2, cannula head 102 includes cannula base 112 and cannula cap 114 which is releasably mounted to the cannula base 112. Any arrangement for mounting cannula cap 114 to cannula base 112 are envisioned including, but not limited to, adhesives, cements, bayonet coupling, frictional fit, snap fit or the like. Cannula head 102 defines first and second head segments 116, 118. First head segment 116 defines a substantially circular cross-sectional dimension transverse to the longitudinal axis "k". In one embodiment, the maximum dimension or diameter of first head segment 116 ranges from about 5 millimeters (mm) to about 15 millimeters (mm), more preferably, about 8 millimeters (mm) to about 12 millimeters (mm). The maximum dimension or diameter of second head segment 118 ranges from about 3 millimeters (mm) to about 12 millimeters (mm), more preferably, about 5 millimeters (mm) to about 8 millimeters (mm). This dimensioning provides a substantially reduced profile to cannula head 102 relative to conventional cannula assemblies thereby occupying substantially less space within compressible port 50.

Still referring to FIG. 2, cannula base 112 defines outer peripheral shelf 120 extending orthogonal to longitudinal axis "k", a second step or shelf 122 inward of the outer annular shelf 120 and annular mounting recess 124 which is disposed inward of the second shelf 122. Cannula base 112 further define insufflation port 126 which depends radially outwardly from second head segment 118. Insufflation port 126 permits the introduction and/or release of insufflation gases through longitudinal passage 110 of cannula assembly 100. The disposition of insufflation port 126 adjacent second head segment 118 results in only a slight extension of the insufflation port 126 beyond the perimeter of first head segment 116. In particular, insufflation port 126 extends a distance "d" beyond first head segment 116. Distance "d" is substantially negligible ranging from about 1 millimeter (mm) to about 3 millimeter (mm) thereby also minimizing the profile of cannula head 102 within the operative region and the potential of obstruction of the cannula base 112 with activities, tasks performed during the surgical procedure. Insufflation port 126 may be supplied with insufflation plug 128 which is selectively positionable within the insufflation port 126. Insufflation plug 128 may be fabricated from a suitable polymeric, elastomeric or foam material and is intended to close the insufflation port 126 to prevent leakage of insufflation gases. Insufflation plug 128 defines flat plug head 130 and plug extension 132 which is received within insufflation port 126. Plug extension 132 is dimensioned to establish a sealing relation with the internal surface area of insufflation port 126.

With reference still to FIG. 2, cannula cap 114 defines central opening 134 having an internal dimension or diameter approximating the internal diameter of cannula sleeve 104. The outer diameter of dimensioning of cannula cap 114 generally approximates the outer diameter of cannula base 112 as shown. Cannula cap 114 defines outer peripheral shelf 136, second shelf 138 disposed radially inward of the peripheral shelf 136 and annular mounting recess 140 which is inward of the second shelf 138. Outer peripheral shelf 136 and second shelf 138 of cannula cap 114 reside on respective outer peripheral shelf 120 and second shelf 122 of cannula base 112 when in the assembled condition of the components. Cannula cap 114 and cannula base 112 may be adhered along respective shelves to secure the two components to each other.

Cannula head 102 includes object seal 142 and zero closure valve 144. Object seal 142 may be any seal adapted to form or establish a sealing relation with a surgical instrumentation introduced through cannula assembly 100. In one embodiment, object seal 142 is a septum seal defining inner seal segment 146 having central aperture 148. Inner seal segment 146 defines a cross-sectional dimension or thickness which gradually decreases toward central aperture 148 and longitudinal axis "k". Object seal 142 may be fabricated from a suitable elastomeric material, gel material, foam material or a fluid filled cavity, having sufficient compliance to form a seal about the surgical instrumentation. Object seal 142 preferably comprises a resilient material in at least the region of inner seal segment 146 to form a substantial seal about an instrument inserted through central aperture 148. Object seal 142 may be monolithically formed or composed of several components interconnected to each other. In one embodiment, object seal 142 includes a resilient elastomer (e.g., polyisoprene or natural rubber) and has a layer of fabric impregnated on each surface of the resilient seal. The fabric may be of any suitable fabric for example, a SPANDEX material containing about 20% LYCRA and about 80% NYLON available from Milliken. A suitable object seal is disclosed in commonly assigned U.S. Pat. No. 6,702,787 to Racenet et al. and/or U.S. Pat. No. 6,482,181 to Racenet et al., the entire contents of each disclosure being incorporated herein by reference. Object seal 142 includes peripheral flange 150 extending in a proximal or trailing direction. Flange 150 is dimensioned to be received within annular mounting recess 140 of cannula cap 114 to facilitate securement of object seal 142 within cannula head 102.

Zero closure valve 144 is mounted adjacent object seal 142 and may be in contacting relation with the object seal 142. Zero closure valve 144 may be any valve adapted to close in the absence of the surgical object and/or in response to the pressurized environment of the underlying insufflated body cavity. Zero closure valve 144 may be a duck bill valve, trumpet valve, gel seal, foam seal, bladder seal or the like. In one embodiment, zero closure valve 144 includes outer peripheral flange 152 depending in a leading or distal direction. Flange 152 is received within corresponding annular 124 recess of cannula base 112 to facilitate securement of the zero closure valve 144 within cannula head 102.

Cannula head 102 is assembled by positioning zero closure valve 144 adjacent cannula base 112 with peripheral flange 152 being received within annular mounting recess 124 of the cannula base 112. Zero closure valve 144 is placed in, e.g., superposed relation, with object seal 142. Cannula cap 114 is positioned on cannula base 112 with peripheral flange 150 of object seal 142 being received within annular mounting recess 140 of cannula cap 114. Cannula cap 114 is then secured relative to cannula base 112 by any of the aforementioned means including, e.g., adhering the cannula cap 114 and the cannula base 112 along respective shelves.

Figure 3:
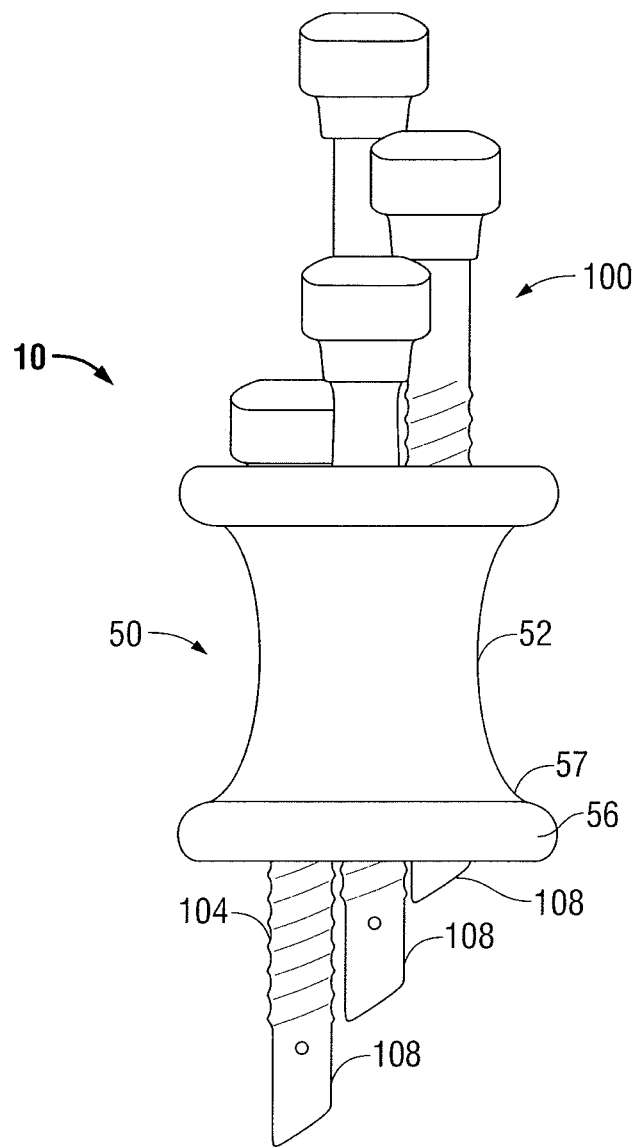
FIG. 3 is a side view of the access assembly of FIG. 1 with the cannula assemblies in a staggered configuration.

Turning now to FIG. 3, cannula assemblies 100 are received through compressible port 50 in a staggered configuration. As noted above, when rigid cannula assemblies are used, the cannula assemblies must be staggered to misalign cannula heads 102 to provide the spacing necessary spacing for the cannula assemblies through compressible port 50. In this manner, distal ends 108 of cannula assemblies 100 extend at various lengths from distal end 57 of compressible port 50.

Figure 4:
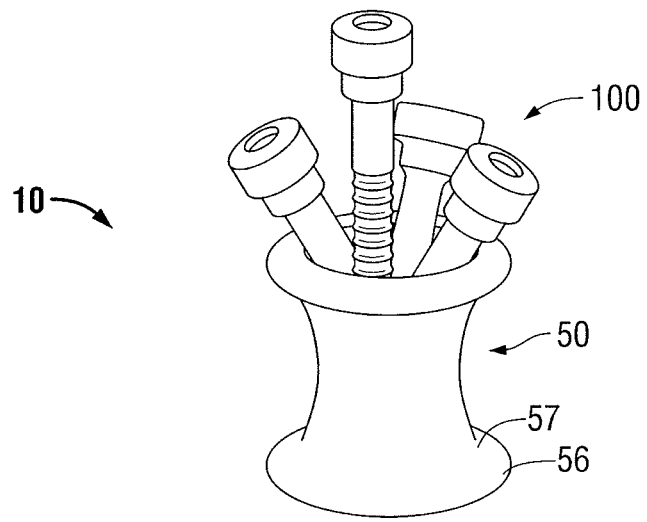
FIG. 4 is a perspective side view of the access assembly of FIG. 1 with the cannula assemblies in an aligned configuration.
Figure 5:
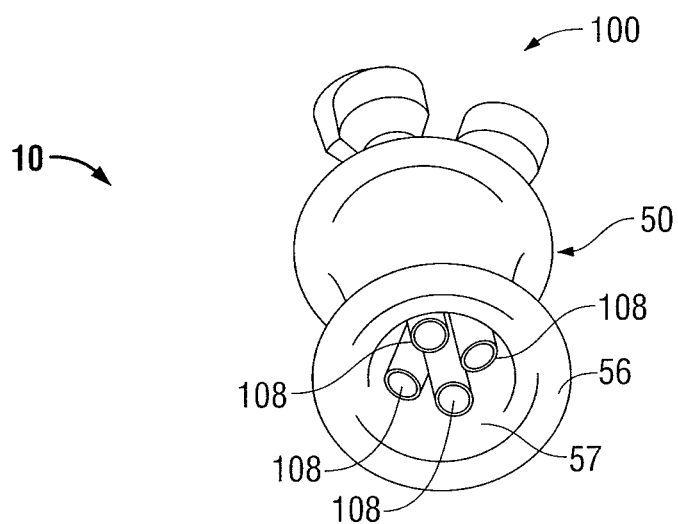
FIG. 5 is a perspective bottom view of the access assembly of FIG. 4.

With reference now to FIGS. 4 and 5, the flexible nature of cannula assemblies 100 permits the flexion thereof. This flexibility allows cannula heads 102 of cannula assemblies 100 to be deflected away from each other, thereby permitting, if desirable, longitudinal alignment of the cannula heads 102 while received within compressible port 50. In this manner, distal ends 108 of cannula assemblies 100 are aligned and extend equally from distal end 57 of compressible port 50. As seen in FIG. 5, in one embodiment, the distal ends of cannula assemblies 100 do not extend beyond lower rim 56 on distal end 57 of compressible port 50 or are substantially flush with the distal face of the compressible port. The aligned configuration of the distal ends of cannula assemblies 100 may increase the range of motion of instruments inserted therethrough by eliminating or reducing the amount of "sword-fighting" that typically occurs when elongated instruments of cannulas are positioned in close proximity to each other.

With reference to FIGS. 1-5, in use, compressible port 50 is compressed for insertion through an incision or opening into a body cavity. Release of the compressive force on port 50 permits port 50 to expand within the opening, thereby sealing the opening and providing access to the body cavity. Cannula assemblies 100 are then inserted through lumen 51 extending through compressible port 100. The flexible nature of cannula assemblies 100 is such that cannula assemblies 100 may be inserted in a staggered fashion (FIG. 3) or with the distal ends thereof aligned (FIGS. 4 and 5).

Once compressible port 50 has been received through an opening and cannula assemblies 100 have been properly positioned therein, a surgeon may perform a procedure through access assembly 10 in a conventional manner. The flexible nature of cannula assemblies 100 permit instruments of various shapes and configurations to be inserted through access assembly 10. In this manner, a surgeon is provided with a greater array of instrumentation and/or a larger range of motion with which to manipulate the instrument. Once the procedure is complete, cannula assemblies 100 may be removed from within compressible port 50, followed by removal of compressible port 50 from within the opening. Alternatively, both cannula assemblies 100 and compressible port 50 may be removed simultaneously. In addition, according to one embodiment, the compressible port may be positioned in an incision or opening within a sleeve, e.g., a surgical retraction sleeve, so as to enable the port to be temporarily removed for specimen removal or the like. If an incision has been created to access the body cavity, it may be closed in a conventional manner.

Figure 6:
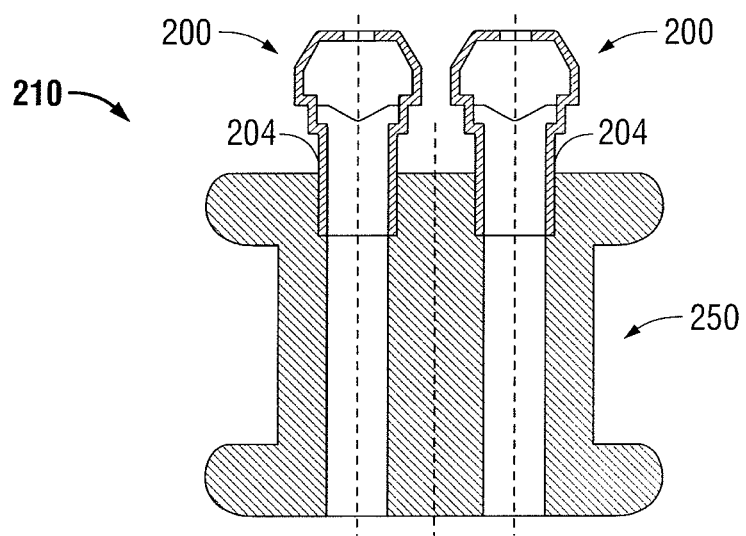
FIG. 6 is a cross-sectional side view of an alternate embodiment of an access assembly according to the present disclosure.
Figure 7:
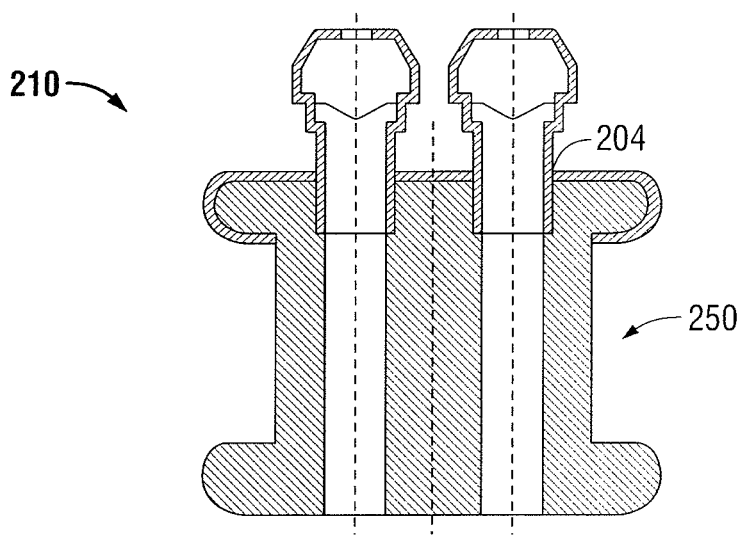
FIG. 7 is a cross-sectional side view of another embodiment of an access assembly according to the present disclosure.

With reference now to FIGS. 6 and 7, which illustrates an alternative embodiment of the invention, compressible port 250 and cannula assembles 200 are securely attached to one another to form access assembly 210. Compressible port 250 and cannula assemblies 200 are substantially similar to compressible port 50 and cannula assemblies 200, respectively, described herein above, and will on therefore, only be described as relates to the differences therebetween.

With continued reference to FIGS. 6 and 7, cannula sleeves 204 are configured to extend only partially within compressible port 250 and are securely retained therein. Cannula assembly may be secured to compressible port 250 using glues, adhesive, welding, bonding, mechanical fasteners and other suitable techniques. Alternatively, cannula assemblies 200 are over-molded to compressible port 250 (FIG. 7) using various techniques. Reducing the length of cannula sleeve 204 permits the use of instruments of curved or bent configurations through access assembly 210. Additionally, a surgeon may be able to manipulate an instrument or instruments inserted through access assembly 210 with a greater range of motion. Furthermore, less material is used to construct cannula assemblies 200, therefore, the cost of material is reduced. In addition, the one-piece construction of access assembly 210 reduces insertion and removal time as both compressible port 250 and cannula assemblies 200 are inserted simultaneously and removed simultaneously, thereby reducing the time to complete and the number of steps involved in the procedure.

It will be understood that various modifications may be made to the embodiments disclosed herein. For example, as noted hereinabove, the diameters or configuration of the disclosed cannula assemblies need not be identical but may be varied depending upon the contemplated surgical instruments to be utilized therethrough. Therefore, the above description should not be construed as limiting, but merely as exemplifications of particular embodiments. Those skilled in the art will envision other modifications within the scope and spirit of the claims appended hereto.

The invention claimed is:

1. An access assembly for insertion through tissue, the access assembly comprising:
   a compressible port having a proximal end and a distal end, the compressible port having a longitudinal lumen extending from the proximal end to the distal end and an upper rim at the proximal end; and
   a flexible cannula assembly mounted at only the proximal end of the compressible port, the flexible cannula assembly being configured to receive an instrument inserted therethrough in a sealing manner, wherein the flexible cannula assembly extends partially into the longitudinal lumen and a distal end of the flexible cannula assembly is longitudinally spaced from the distal end of the compressible port,
   wherein at least a portion of the flexible cannula assembly is overmolded to and extends over a periphery of the upper rim.

2. The access assembly as recited in claim 1, wherein the flexible cannula assembly is securely attached to the compressible port.

3. The access assembly as recited in claim 1, wherein the compressible port includes a parylene coating.

4. The access assembly as recited in claim 1, wherein the flexible cannula assembly includes a seal configured to seal the longitudinal lumen in the absence of an instrument being inserted therethrough.

5. The access assembly as recited in claim 1, wherein the flexible cannula assembly includes zero-closure or duck-bill seals.

6. The access assembly as recited in claim 1, further comprising a plurality of flexible cannula assemblies, wherein each of the plurality of flexible cannula assemblies is securely attached to the compressible port.

7. The access assembly as recited in claim 1, wherein the flexible cannula assembly is attached to the compressible port using at least one of glue, adhesive or mechanical fasteners.

8. The access assembly as recited in claim 1, wherein the compressible port includes at least one portion that is foam.

9. The access assembly as recited in claim 8, wherein the compressible port comprises a foam central portion positioned between the proximal end of the compressible port and the distal end of the compressible port.

* * * * *